United States Patent
Lorenzo et al.

(10) Patent No.: US 11,992,241 B2
(45) Date of Patent: May 28, 2024

(54) SYSTEM TO ASSIST DELIVERY OF A MECHANICAL INTRAVASCULAR TREATMENT DEVICE

(71) Applicant: DePuy Synthes Products, Inc., Raynham, MA (US)

(72) Inventors: Juan Lorenzo, Davie, FL (US); Massod Siddiqui, Irvine, CA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 811 days.

(21) Appl. No.: 16/778,517

(22) Filed: Jan. 31, 2020

(65) Prior Publication Data
US 2021/0236165 A1 Aug. 5, 2021

(51) Int. Cl.
| | |
|---|---|
| A61B 17/34 | (2006.01) |
| A61F 2/95 | (2013.01) |
| A61B 17/00 | (2006.01) |
| A61M 25/00 | (2006.01) |

(52) U.S. Cl.
CPC ............ *A61B 17/3468* (2013.01); *A61F 2/95* (2013.01); *A61F 2/9517* (2020.05); *A61B 2017/00292* (2013.01); *A61M 2025/0042* (2013.01)

(58) Field of Classification Search
CPC ....... A61B 17/3468; A61B 2017/00292; A61F 2/9517
See application file for complete search history.

(56) References Cited

U.S. PATENT DOCUMENTS

| | | | |
|---|---|---|---|
| 5,201,757 A | 4/1993 | Heyn et al. | |
| 5,433,723 A * | 7/1995 | Lindenberg | A61F 2/95 606/198 |
| 5,441,516 A * | 8/1995 | Wang | A61F 2/95 606/198 |
| 5,634,928 A * | 6/1997 | Fischell | A61F 2/958 623/1.11 |
| 5,776,142 A * | 7/1998 | Gunderson | A61F 2/88 606/198 |

(Continued)

FOREIGN PATENT DOCUMENTS

WO 2005079151 A2 9/2005

OTHER PUBLICATIONS

European Search Report for counterpart EP Patent Application (dated Sep. 2, 2021)(9 pp.).

*Primary Examiner* — Alexander J Orkin
(74) *Attorney, Agent, or Firm* — TROUTMAN PEPPER HAMILTON SANDERS LLP

(57) ABSTRACT

A system to assist delivery of a mechanical intravascular treatment device, wherein the system includes a first assist device having a first linear sliding mechanism. The linear sliding mechanism includes: a first non-slidable section; a first slidable section linearly displaceable relative to the first non-slidable section; and a first tension device connected to the first slidable section to move together; the first tension device being transitionable between an unsecured state and a secured state. A first securing hub is fixedly attached to the first non-slidable section, wherein the first securing hub is transitionable between an unsecured state and a secured state. The system may also include a second assist device. The assist devices provide enhanced control of movement of the delivery wire and/or guide catheter.

18 Claims, 12 Drawing Sheets

(56) References Cited

U.S. PATENT DOCUMENTS

| | | | |
|---|---|---|---|
| 5,868,755 A * | 2/1999 | Kanner | A61F 2/958 606/198 |
| 6,143,021 A * | 11/2000 | Staehle | A61F 2/95 606/108 |
| 6,146,415 A * | 11/2000 | Fitz | A61F 2/95 606/171 |
| 6,419,679 B1 * | 7/2002 | Dhindsa | A61B 17/221 606/127 |
| 7,758,625 B2 | 7/2010 | Wu et al. | |
| 7,892,186 B2 | 2/2011 | Soukup et al. | |
| 9,326,872 B2 | 5/2016 | Sokel | |
| 9,375,216 B2 | 6/2016 | Tal et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,213,301 B2 | 2/2019 | Ganesan et al. | |
| 2006/0265045 A1 | 11/2006 | Shiu et al. | |
| 2007/0156222 A1 * | 7/2007 | Feller, III | A61F 2/95 623/1.11 |
| 2009/0030496 A1 * | 1/2009 | Kaufmann | A61F 2/966 623/1.11 |
| 2009/0105798 A1 * | 4/2009 | Koch | A61F 2/95 623/1.11 |
| 2009/0182405 A1 * | 7/2009 | Arnault De La Menardiere | A61F 2/954 623/1.11 |
| 2011/0288558 A1 * | 11/2011 | Nimgaard | A61F 2/95 606/108 |
| 2014/0018732 A1 | 1/2014 | Bagaoisan et al. | |
| 2015/0045871 A1 * | 2/2015 | Beckham | A61F 2/966 623/1.11 |
| 2015/0305863 A1 * | 10/2015 | Gray | A61F 2/2436 623/2.11 |
| 2016/0008153 A1 * | 1/2016 | Mangiardi | A61F 2/95 623/1.11 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0042678 A1 * | 2/2017 | Ganesan | A61B 1/00148 |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |
| 2017/0312109 A1 | 11/2017 | Le | |

(56) References Cited

U.S. PATENT DOCUMENTS

| | | |
|---|---|---|
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2019/0201222 A1 | 4/2019 | Nimgaard |
| 2019/0167456 A1 | 6/2019 | Collins et al. |
| 2019/0209356 A1 | 7/2019 | Collins et al. |

\* cited by examiner

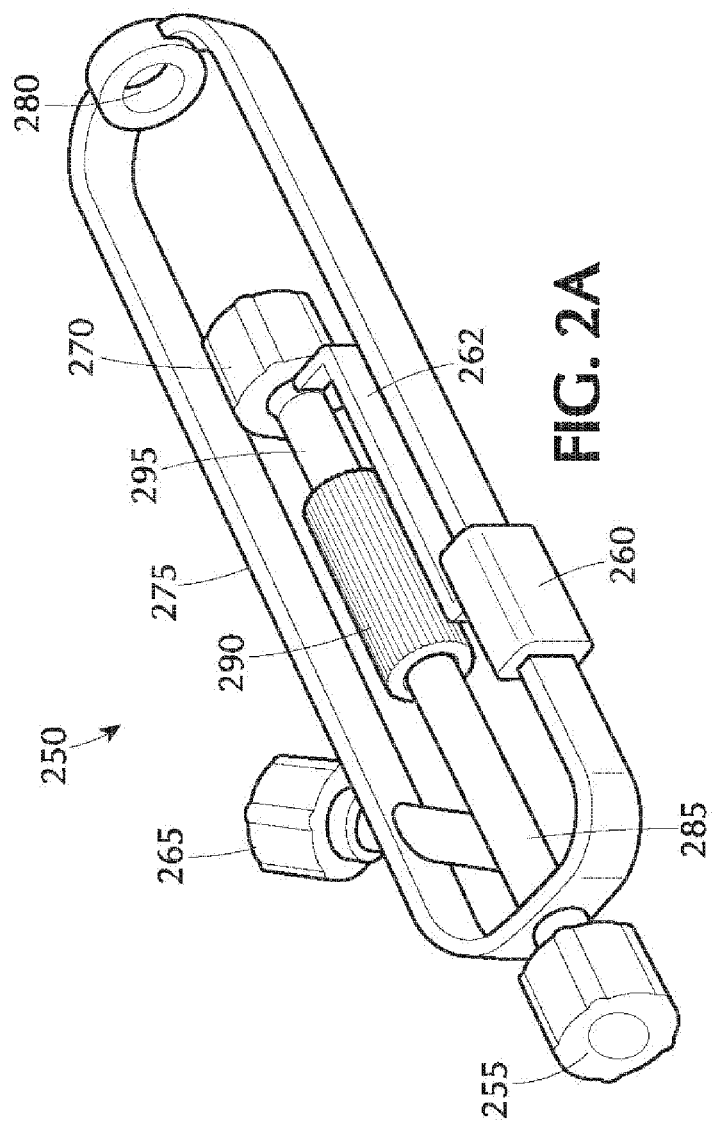

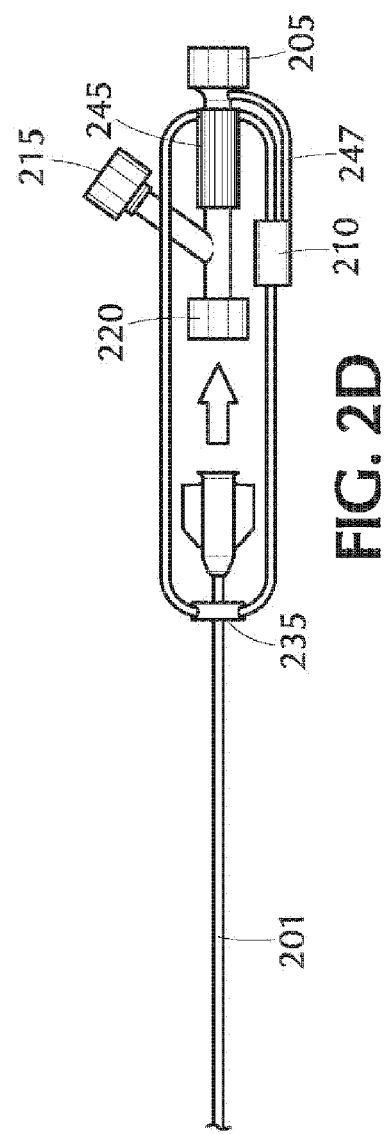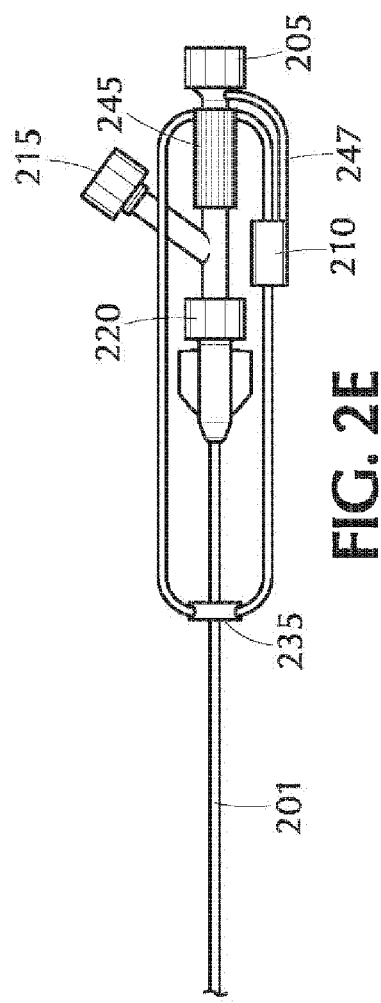

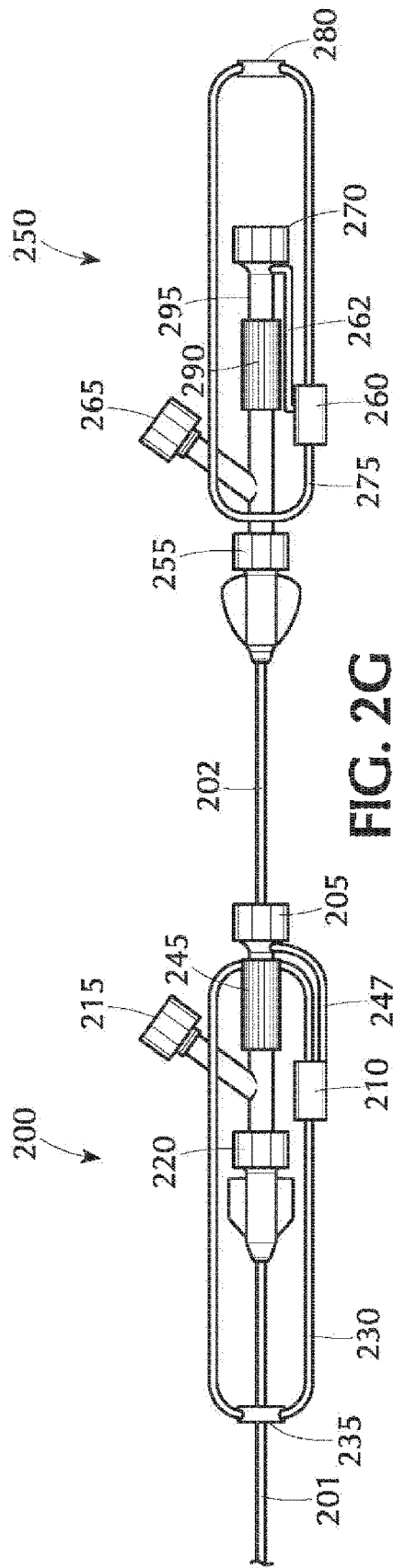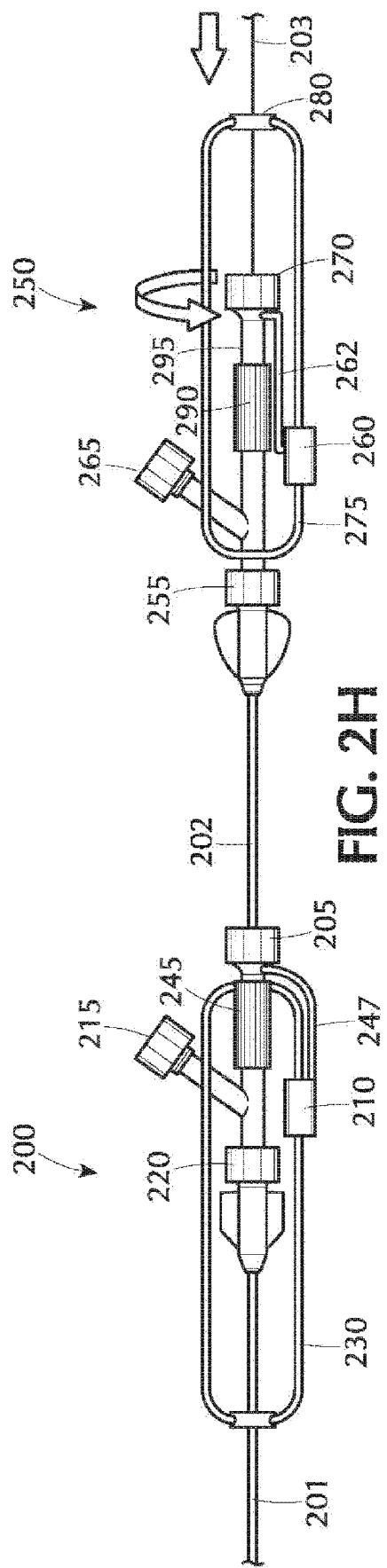

SYSTEM TO ASSIST DELIVERY OF A MECHANICAL INTRAVASCULAR TREATMENT DEVICE

FIELD OF THE INVENTION

The present invention relates to a system to assist in delivery (e.g., deployment, recapture) of a mechanical intravascular treatment device (e.g., a braided flow diverter). In particular, the present invention is directed to a system to assist delivery of a mechanical intravascular treatment device that is capable of providing additional force during navigation through a tortuous vessel and/or enhanced control for precise positioning of the device at a target site in the vessel.

DESCRIPTION OF RELATED ART

Mechanical intravascular treatment devices, for example, braided flow diverters and other self-expanding stent devices, are advanced intravascularly through the body to a target location using a plurality of ancillary devices (e.g., a guide catheter, a microcatheter, and a delivery wire) in the treatment of aneurysms. Once the microcatheter and mechanical intravascular treatment device have been positioned within the vessel at the target site, the self-expanding stent is deployed (unsheathed) to an expanded state diverting blood flow away from the aneurysm. The deployment of such self-expanding mechanical vascular devices requires significant dexterity and coordinated, complex "push-pull" hand manipulation by the interventionalist's using both hands simultaneously that is not natural, comfortable or ergonomic. In essence, such hand manipulation for deployment of the self-expanding mechanical intravascular treatment device requires the interventionalist to push on the delivery wire while holding the hub of the delivery microcatheter with one hand, while simultaneously with the other hand pull back (i.e., unsheathe) the microcatheter from the self-expanding mechanical vascular device allowing it to automatically expand/enlarge at the target site making physical contact with the inner walls of the vessel. In addition to the orchestration of complex independent movements of both hands simultaneously, relatively high forces may be required to counter the friction experienced in deploying and thereafter recapturing flow diverters when advancing though tortuous pathways. In the case of a challenging anatomy, an assistant may be required to aid the interventionalist. Even if the interventionalist alone is able to deploy and/or recapture the self-expanding mechanical vascular device, because of such complex, unnatural hand manipulations it is difficult to have refined control with any degree of accuracy.

It is therefore desirable to develop a system to assist in delivery (e.g., deployment and/or recapture) of a mechanical intravascular treatment device that allows for such complex motion in a more ergonomic, natural manner while providing enhanced control and imparting additional force, if necessary.

SUMMARY OF THE INVENTION

An aspect of the present invention is directed to a system to assist in delivery (e.g., deployment and/or recapture) of a mechanical intravascular treatment device that allows for complex motion in a more ergonomic, natural manner while providing enhanced control and imparting additional force, if necessary.

Another aspect of the present invention relates to a system to assist delivery of a mechanical intravascular treatment device, wherein the system includes a first assist device having a first linear sliding mechanism. The linear sliding mechanism includes: a first non-slidable section; a first slidable section linearly displaceable relative to the first non-slidable section; and a first tension device connected to the first slidable section to move together; the first tension device being transitionable between an unsecured state and a secured state. A first securing hub is fixedly attached to the first non-slidable section, wherein the first securing hub is transitionable between an unsecured state and a secured state.

While still another aspect of the present invention is directed to a system to assist delivery of a mechanical intravascular treatment device, wherein the system is configured so that the first tension device receives and secures therein a delivery wire, while the first securing hub receives and secures therein a microcatheter. When the first tension device and the first securing hub are both in the secured state, controlled linear movement of the delivery wire while maintaining in place the microcatheter is achievable using the first linear sliding mechanism.

Yet another aspect of the present invention relates to a system to assist delivery of a mechanical intravascular treatment device, wherein the system is configured so that the first tension device receives and secures therein a microcatheter, while the first securing hub receives and secures therein a guide catheter. When the first tension device and the first securing hub are both in the secured state, controlled linear movement of the microcatheter while maintaining in place the guide catheter is achievable using the first linear sliding mechanism.

A still further aspect of the present invention is directed to a system to assist delivery of a mechanical intravascular treatment device, wherein the system is configured such that the first linear sliding mechanism includes an extension shaft extending from one end of the first non-slidable section, and the first slidable section is telescopically slidable along at least a portion of the extension shaft.

Another aspect of the present invention relates to a system to assist delivery of a mechanical intravascular treatment device, wherein the system is configured such that the first non-slidable section is a first frame having parallel sides and curved opposing ends. The first slidable section being linearly displaceable along a portion of one of the sides of the first frame; wherein the first slidable section includes a first slider tab connected to the tension device via a first connecting arm.

A further aspect of the present invention is directed to a system to assist delivery of a mechanical intravascular treatment device, wherein the system is configured to further include a second assist device having a second linear sliding mechanism. The second linear sliding mechanism includes: a second non-slidable section; a second slidable section; linearly displaceable relative to the second non-slidable section; and a second tension device connected to the second slidable section to move together; the second tension device being transitionable between an unsecured state and a secured state. A second securing hub is fixedly attached to the second non-slidable section; the second securing hub being transitionable between an unsecured state and a secured state.

While a still further aspect of the present invention relates to a system to assist delivery of a mechanical intravascular treatment device, wherein the system is configured such that the first tension device receives and secures therein a delivery wire, while the first securing hub receives and secures therein a microcatheter. When the first tension device and the first securing hub are both in the secured state, controlled linear movement of the delivery wire while maintaining in place the microcatheter is achievable using the first linear sliding mechanism. The system is further configured such that the second tension device receives and secures therein the microcatheter, while the second securing hub receives and secures therein a guide catheter. When the second tension device and the second securing hub are both in the secured state, controlled linear movement of the microcatheter while maintaining in place the guide catheter is achievable using the second linear sliding mechanism.

Yet another aspect of the present invention is directed to a system to assist delivery of a mechanical intravascular treatment device, wherein the system is configured such that the second non-slidable section is a second frame having parallel sides and curved opposing ends. The second slidable section being linearly displaceable along a portion of one of the sides of the second frame; wherein the second slidable section includes a second slider tab connected to the second tension device via a second connecting arm.

While still another aspect of the present invention is directed to a method for using a system to assist delivery of a mechanical intravascular treatment device, wherein the system includes a first assist device having a first linear sliding mechanism. The first linear sliding mechanism includes: a first non-slidable section; a first slidable section linearly displaceable relative to the first non-slidable section; and a first tension device connected to the first slidable section to move together; the first tension device being transitionable between an unsecured state and a secured state. A first securing hub is fixedly attached to the first non-slidable section, wherein the first securing hub is transitionable between an unsecured state and a secured state. During use of the system a delivery wire is advanced though a lumen of a microcatheter until the mechanical vascular treatment device disposed at a distal end of the delivery wire emerges from a distal end of the microcatheter; wherein such advancement is achieved using only the first linear sliding mechanism without grasping any portion of the delivery wire.

Another aspect of the present invention relates to a method for using a system to assist delivery of a mechanical intravascular treatment device, wherein the first tension device receives and secures therein the delivery wire, while the first securing hub receives and secures therein the microcatheter. When the first tension device and the first securing hub are both in the secured state, controlled movement of the delivery wire while maintaining in place the microcatheter is achievable using the first linear sliding mechanism.

While still another aspect of the present invention is directed to a method for using a system to assist delivery of a mechanical intravascular treatment device, wherein the first tension device receives and secures therein the microcatheter, while the first securing hub receives and secures therein the guide catheter. When the first tension device and the first securing hub are both in the secured state, controlled movement of the microcatheter while maintaining in place the guide catheter is achievable using the first linear sliding mechanism.

Yet another aspect of the present invention relates to a method for using a system to assist delivery of a mechanical intravascular treatment device, wherein the first linear sliding mechanism includes an extension shaft extending from one end of the first non-slidable section, and the first slidable section is slidable along at least a portion of the extension shaft.

While another aspect of the present invention is directed to a method for using a system to assist delivery of a mechanical intravascular treatment device, wherein the first non-slidable section is a first frame having parallel sides and curved opposing ends. The first slidable section being linearly displaceable along a portion of one of the sides of the first frame; wherein the first slidable section includes a first slider tab connected to the tension device via a first connecting arm.

Still another aspect of the present invention relates to a method for using a system to assist delivery of a mechanical intravascular treatment device, wherein the system further includes a second assist device having a second linear sliding mechanism. The second linear sliding mechanism includes: a second non-slidable section; a second slidable section; linearly displaceable relative to the second non-slidable section; a second tension device connected to the second slidable section to move together, the second tension device being transitionable between an unsecured state and a secured state. The system further including a second securing hub fixed in position with that of the second non-slidable section; the second securing hub being transitionable between an unsecured state and a secured state. The method of use of the system calls for simultaneously with the advancing step, unsheathing the mechanical intravascular treatment device from the distal end of the microcatheter using only the second linear sliding mechanism without grasping any portion of the microcatheter.

Another aspect of the present invention is directed to a method for using a system to assist delivery of a mechanical intravascular treatment device, wherein the first tension device receives and secures therein the delivery wire, while the first securing hub receives and secures therein the microcatheter. When the first tension device and the first securing hub are both in the secured state, controlled linear movement of the delivery wire while maintaining in place the microcatheter is achievable using the first linear sliding mechanism. The second tension device receives and secures therein the microcatheter, while the second securing hub receives and secures therein a guide catheter. When the second tension device and the second securing hub are both in the secured state, controlled linear movement of the microcatheter while maintaining in place the guide catheter is achievable using the second linear sliding mechanism.

Still another aspect of the present invention relates to a method for using a system to assist delivery of a mechanical intravascular treatment device, wherein the second non-slidable section is a second frame having parallel sides and curved opposing ends; the second slidable section being linearly displaceable along a portion of one of the sides of the second frame; wherein the second slidable section includes a second slider tab connected to the second tension device via a second connecting arm.

A still further aspect of the present invention is directed to a method for using a system to assist delivery of a mechanical intravascular treatment device, wherein the first linear sliding mechanism associated with the advancing step and the second linear sliding mechanism associated with the unsheathing step are carried out by movement in respective directions towards one another to deploy the mechanical intravascular treatment device.

One additional aspect of the present invention relates to a method for using a system to assist delivery of a mechanical intravascular treatment device, wherein the first linear sliding mechanism associated with the advancing step and the second linear sliding mechanism associated with the unsheathing step are carried out by movement in opposite directions from one another to recapture the mechanical intravascular treatment device within the microcatheter.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 2A is a first assist device of an assist system in accordance with a second embodiment of the present invention assembled to a first rotating hemostatic valve for controlled advancement ("pushing") of a delivery wire with a mechanical intravascular treatment device disposed at the distal end thereof using a first linear sliding mechanism while maintaining in place the microcatheter;

FIG. 2D depicts insertion of a proximal end of the guide catheter through the guide catheter receiving passageway of the second assist device of FIG. 2B;

FIG. 2E depicts securing the proximal end of the inserted guide catheter in the guide catheter securing hub of the second rotating hemostatic valve associated with the second assist device of FIG. 2B (while the second linear sliding mechanism of the second assist device is fully retracted ("pushed in") towards the guide catheter receiving passageway);

FIG. 2G depicts attaching a proximal end of the microcatheter to the microcatheter securing hub of the first assist device of FIG. 2A (while the first linear sliding mechanism is fully extended ("pulled out") a maximum distance between the microcatheter securing hub and the delivery wire tension device) securing the microcatheter therein;

FIG. 2H depicts loosening the delivery wire tension device of the first assist device to allow for insertion therein of the delivery wire with the mechanical intravascular treatment device disposed at its distal end; positioning the mechanical intravascular treatment device at a target site; tightening the delivery wire tension device to secure the delivery wire in place;

FIG. 2I depicts two handed use of the assembled first and second assist device along with their respective first and second rotating hemostatic valves in accordance with the second embodiment of the present inventive assist system; that is, unsheathing ("pulling back") the distal end of the microcatheter from the mechanical intravascular treatment device with the left hand by manipulating the second linear sliding mechanism of the second assist device, while simultaneously advancing ("pushing") the delivery wire with the mechanical intravascular treatment device disposed at its distal end with the right hand by manipulating the first linear sliding mechanism of the first assist device.

DETAILED DESCRIPTION OF THE INVENTION

Figure 1A:
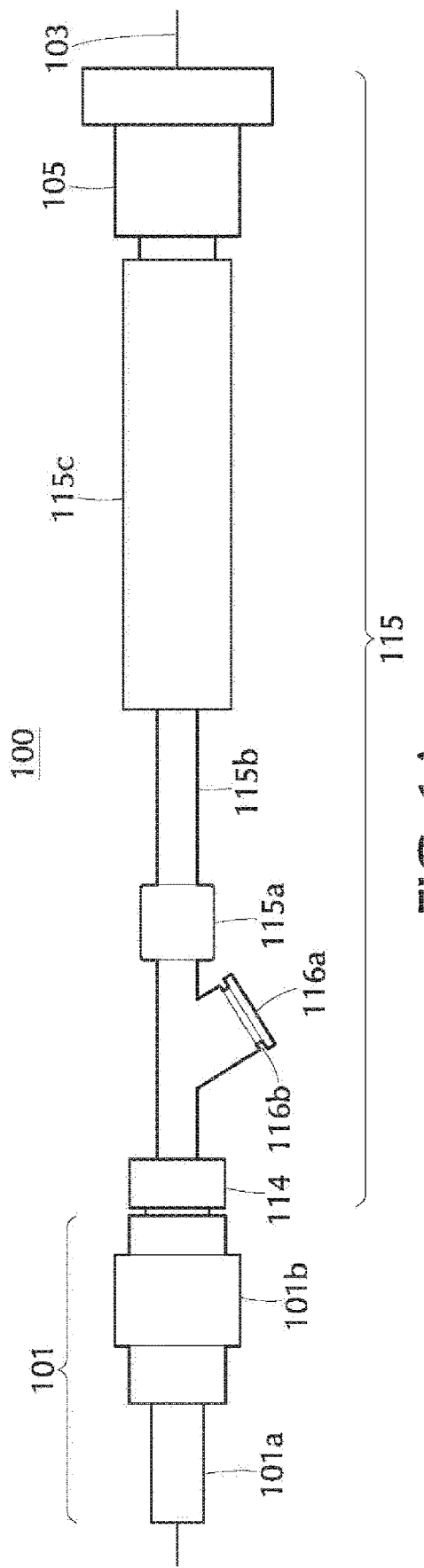
FIG. 1A illustrates a schematic view of an assist device in accordance with a first embodiment of the present inventive system for assisting in delivery of a mechanical intravascular treatment device; the assist device is a linear sliding mechanism connected to the proximal end of a microcatheter; wherein a delivery wire is advanced through a lumen of the microcatheter using only the linear sliding mechanism.

The terms "distal" or "proximal" are used in the following description with respect to a position or direction relative to the treating physician or medical interventionalist. "Distal" or "distally" are a position distant from or in a direction away from the physician or interventionalist and closest to or a direction towards the target site to be treated in the vessel. "Proximal" or "proximally" or "proximate" are a position near or in a direction toward the physician or medical interventionist and distance from or in a direction away from the target site to be treated in the vessel. The terms "occlusion", "clot" or "blockage" are used interchangeably.

The present invention is directed to a device to assist during delivery (e.g., deployment and/or recapture) of a mechanical intravascular treatment device (e.g., automatic self-expanding stent) employing a guide catheter, a microcatheter and a delivery wire (e.g., pusher wire) and other possible auxiliary devices. Various mechanical configurations may be used to produce the linear movement generated by the linear sliding mechanism employed with the first and/or second assist devices of the present inventive assist system and are not limited by the exemplary configurations illustrated and described. Other configurations of the linear sliding mechanism are contemplated and within the intended scope of the present invention.

The present inventive assist system may include: (i) a single assist device to aid in the controlled movement of the unsheathing ("pulling back") of a microcatheter; (ii) a single assist device to aid in the controlled advancement ("pushing") of a delivery wire having a mechanical intravascular treatment device disposed at a distal end thereof; or (iii) both assist devices used simultaneously by the interventionalist, one manipulated with each hand. By way of illustrative example, FIGS. 1A-1E illustrate an assist system in accordance with a first embodiment of the present invention comprising only a single or first assist device to aid in delivery of a mechanical intravascular treatment device. Whereas, exemplary FIGS. 2A-2I illustrate an assist system in accordance with a second embodiment of the present invention including two assist devices (one associated with each hand) employed simultaneously. One assist device controls movement during unsheathing of a distal end of the microcatheter from the mechanical intravascular treatment device (i.e., the "pulling back" operation), simultaneously a separate assist device aids in independent delivery (i.e., the "pushing" operation) of a delivery wire having a mechanical intravascular treatment device arranged at a distal end thereof. FIG. 3 shows yet a third embodiment of the present inventive assist system employing two assist devices simultaneously in which linear movement is achieved via rotating dial (e.g., thumbwheel). It is contemplated and within the intended scope of the present invention for the present inventive assist system to be configured as only a single assist device to aid in delivery/control of a single device (e.g., a "pulling back" of a microcatheter or "pushing" of a delivery wire) or two assist devices operated simultaneously, wherein each assist device is used to aid in independent operation of controlled movement of a device.

FIG. 1A is a side view of a first embodiment of the present inventive assist system comprising only a single assist device 100 for aiding in delivery, deployment and/or recapture of a mechanical vascular treatment device, for example, an automatically self-expanding stent. Starting from a proximal end (i.e., farthest from the target vascular site to be treated (e.g., an aneurysm)) and advancing in a distal direction towards the opposite distal end (i.e., closest to the target vascular site to be treated), the assist device 100 preferably includes a linear sliding mechanism 115 directly connected to a proximal end of a microcatheter 101 via a securing hub 114 (e.g. male connector either fixed or rotating). Microcatheter 101 includes a microcatheter hub 101b secured or assembled to a microcatheter shaft 101a. A fluid or irrigation port 116a and associated fixed female connector luer 116b may be provided for dispensing a fluid (e.g., saline solution) therethrough. Leakage of fluid is prevented by a plurality of seals, namely: (i) a ring seal (e.g., O-ring) 111 disposed radially between the extension shaft 115b and sliding section 115c; and (ii) a compression seal 105a located at the axial interface between the sliding section 115c and the delivery wire tension device 105.

Specifically, the linear sliding mechanism 115 includes a delivery wire tension device (e.g., rotating valve) 105, a slidable section 115c telescopically slidable along an extension shaft 115b that, in turn, is fixedly mounted to a non-slidable section 115a serving as a stop element to limit or restrict movement of the slidable section 115c. Delivery wire tension device 105 is transitionable, preferably by rotation, between an unlocked/released/open/loosened state and a locked/secured/closed/tensioned state about a delivery or pusher wire 103. While in an unlocked/released/open/loosened state the delivery or pusher wire 103 is freely insertable, slidable or advanceable through an axial opening/lumen of the delivery wire tension device 105; while in a locked/secured/closed/tensioned state, the delivery wire tension device 105 is secured about the delivery wire 103 preventing displacement of the two components relative to one another. A proximal end of the slidable section 115c is fixedly connected/secured to the distal end of delivery wire tension device 105 so that the two components simultaneously move linearly together along the extension shaft 115b.

Figure 1B:
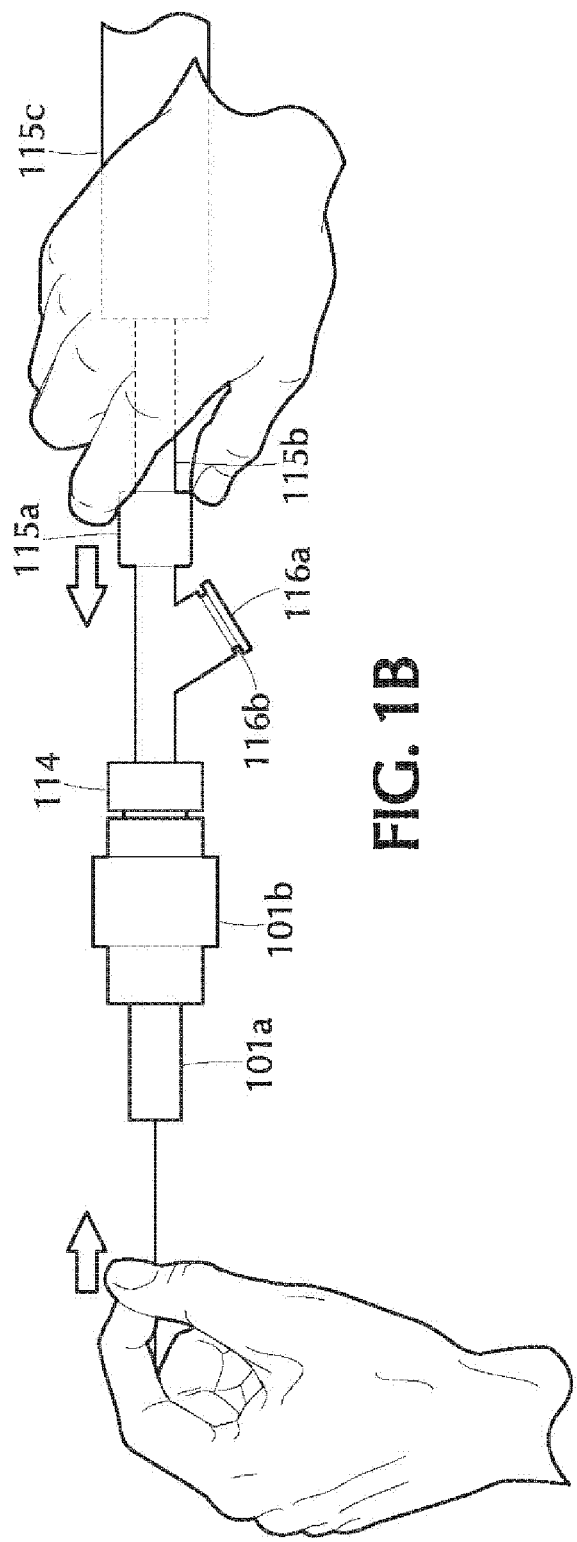
FIG. 1B illustrates the right and left hands of the interventionalist during deployment of a mechanical intravascular treatment device; wherein the right-hand controls advancement ("pushing") of the delivery wire with the mechanical intravascular treatment device disposed at its distal end using only the linear sliding mechanism of the assist device of FIG. 1A, without directly physically contacting the delivery wire itself.
Figure 1C:
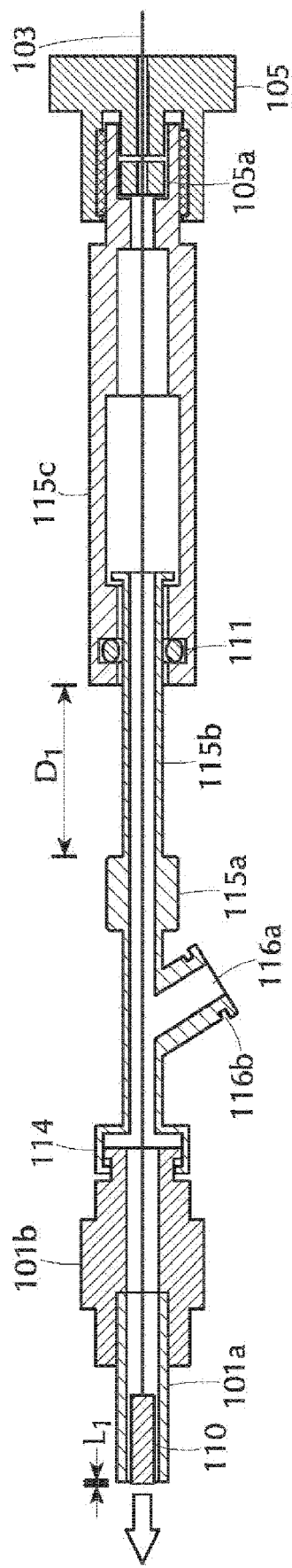
FIG. 1C is a longitudinal cross-sectional view of the assist device of FIG. 1A, wherein the linear sliding mechanism is depicted in a fully extended position.

In a preferred embodiment, initially (in the absence or free of any externally applied mechanical force applied in a distal direction), the slidable section 115c is in its fully extended position or state (i.e., maximum linear displacement $D_1$ between the non-slidable section 115a and the slidable section 115c; and minimum length $L_1$ of delivery wire 103 unsheathed from the microcatheter 101), as shown in FIG. 1C. Non-slidable section 115a acts as a bumper or stop element to restrict or limit linear displacement of the slidable section 115c in a distal direction.

Figure 1D:
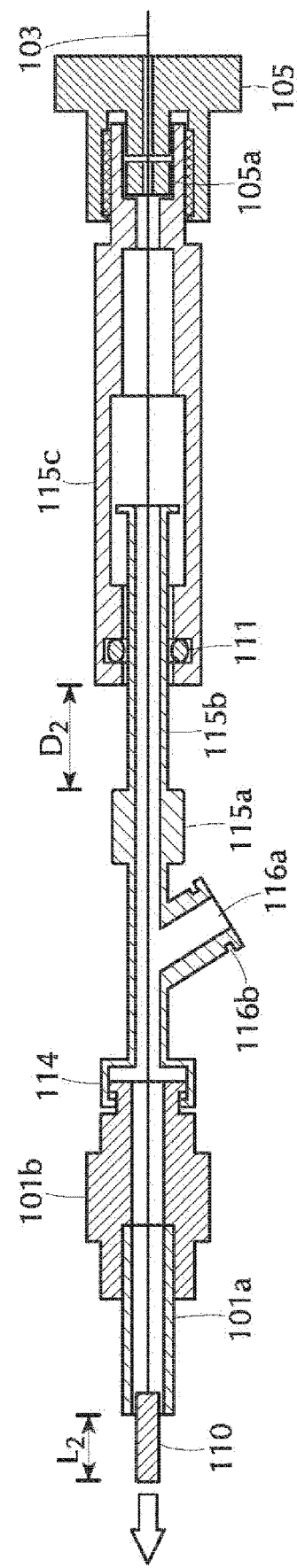
FIG. 1D is a longitudinal cross-sectional view of the assist device of FIG. 1A, wherein the linear sliding mechanism is depicted in a position approximately midway between the fully extended position of FIG. 1C and fully retracted position of FIG. 1E.
Figure 1E:
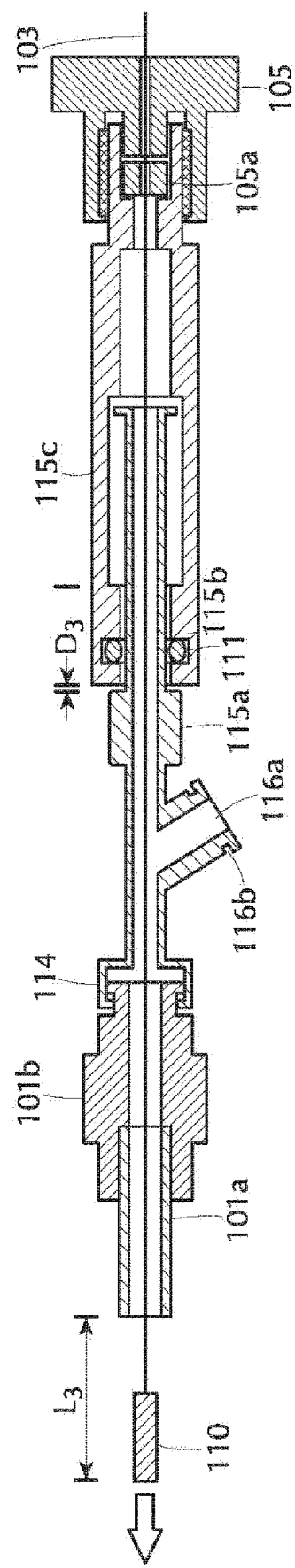
FIG. 1E is a longitudinal cross-sectional view of the assist device of FIG. 1A, wherein the linear sliding mechanism is depicted in a fully retracted position.

During delivery (e.g., deployment or recapture) of the mechanical intravascular treatment device 110, "pushing" or advancing of the delivery wire 103 through the lumen of the microcatheter 101 using the present inventive assist device 100 in FIG. 1A eliminates the need to grasp the delivery wire itself (i.e., without direct finger manipulation of the delivery wire 103 itself). In operation of the first embodiment of the present inventive assist system 100, the microcatheter 101 and mechanical intravascular treatment device 110 disposed in the lumen thereof are properly positioned at the target treatment site using the delivery wire 103. Once properly positioned at the target treatment site, while the slidable section 115c is in a fully extended state (i.e., maximum linear displacement $D_1$ between the non-slidable section 115a and the slidable section 115c; and minimum length $L_1$ of delivery wire 103 unsheathed from the microcatheter 101) as shown in FIG. 1C, delivery wire tension device 105 secured thereto is transitioned (e.g., via rotation) to a secured/closed/tightened/locked state about the delivery wire 103. As the slidable section 115c is displaced linearly along the extension shaft 115b in a distal direction, the delivery wire 103 secured within the delivery wire tension device 105 advances with it (as illustrated in FIGS. 1D & 1E showing displacement approximately midway and fully compressed/retracted positions, respectively). In the fully compressed/retracted position shown in FIG. 1E, minimum linear displacement $D_3$ exists between the non-slidable section 115a and slidable section 115c; while a maximum length $L_3$ of delivery wire 103 is unsheathed from the microcatheter 101.

Referring to FIG. 1B, the mechanical intravascular treatment device 110 is deployed using a single assist device in accordance with this first embodiment of the present inventive assist system. With one hand (e.g., the left hand), the interventionalist unsheathes ("pulls back") the distal end of the mechanical intravascular treatment device 110 by direct hand manipulation of the microcatheter 101 in a proximal direction (i.e., towards the first assist device 100), as indicated by the arrow to the right. Simultaneously, with the other hand (e.g., the right hand) the interventionalist, while grasping the slidable section 115c between the little finger and palm, displaces the slidable section 115c in a distal direction (as indicated by the arrows) towards the non-slidable section 115a (grasped between the thumb and forefinger) thereby advancing ("pushing") with the delivery wire 103 the mechanical vascular treatment device 110 in a distal direction out from the distal end of the microcatheter 101. This combined movement of both hands unsheathes the distal end of microcatheter 101 from the distal end of the delivery wire 103 while simultaneously pushing the self-expanding mechanical intravascular treatment device disposed at the distal end of the delivery wire 103 out from the distal end of the microcatheter 101 causing the mechanical intravascular treatment device to automatically deploy (automatically self-expand to an enlarged diameter) at the target site in the vessel. Use of the present inventive assist device 100 eliminates the need for the interventionalist to directly grasp or hold the delivery wire 103 itself providing refined control of movement and maximizing force required during navigation of tortuous pathways.

The single assist device 100 depicted in FIGS. 1A-1E is employed to assist only one hand (e.g., typically performed using the right hand) of the interventionalist in "pushing" of the self-expanding mechanical intravascular treatment device out from the distal end of the lumen of the microcatheter via the delivery wire. Manual dexterity required to advance the delivery wire through the lumen of the microcatheter while maintaining the microcatheter in place (e.g., typically carried out with the right hand) is more complex and unnatural than the manipulation of the other hand unsheathing the microcatheter from the self-expanding mechanical vascular treatment device while maintaining in place the guide catheter (e.g., typically carried out with the left hand). Alternative embodiments and configurations are contemplated and within the scope of the present invention wherein two assist devices are employed, one for each hand. Such an assist system in accordance with the present invention is shown in FIGS. 2A-2I comprising two assist devices operated simultaneously, each hand of the interventionalist independently manipulating a corresponding assist device.

Referring to FIG. 2A, the present inventive assist system includes a first assist device 250 for use with the one hand (e.g., the right hand) to assist in controlled advancing movement (e.g., "pushing") the self-expanding mechanical intravascular treatment device out from the distal end of the microcatheter using the delivery wire while maintaining in place the microcatheter. A first rotating hemostatic valve or Y-valve includes a microcatheter securing hub 255, an irrigation or fluid port 265, a primary shaft 285, and a connector 290 all in fluid communication with one another. The first rotating hemostatic valve or Y-valve is assembled to a first frame 275 of the first assist device that serves as a first non-slidable section of a first linear sliding mechanism for the interventionalist to easily grasp (as shown in FIG. 2I). In the exemplary illustration, first frame 275 is a closed loop with parallel longitudinal sides and opposing curved ends (resembling a link of a chain), that serves as a handle or grip. The microcatheter securing hub 255 and irrigation port 265 are disposed exteriorly of the first frame 275, while primary shaft 285 and connector 290 are disposed interiorly of the first frame 275. A proximal end of first frame 275 has a delivery wire receiving passageway (e.g., loop or eyelet) 280 defined therein through which a delivery wire is freely passable therethrough. At an opposite distal end of the first frame 275 the microcatheter securing hub 255 disposed exteriorly of the first frame 275 receives and secures therein the microcatheter to prevent linear movement of the microcatheter once the delivery wire is properly positioned at the target site in the vessel. The first linear sliding mechanism further includes a slidable section 260 (e.g., slider or actuator tab) slidable along a portion of one of the longitudinal sides of the first frame 275. Slidable section 260 is connected to the delivery wire tension device 270 via a connecting arm 262, preferably disposed interiorly of the first frame 275. Extension shaft 295 is telescopically slidable within an inner channel or passage of the connector 290 attached to the distal end of the primary shaft 285 opposite that of the microcatheter securing hub 255. The delivery wire tension device 270 is attached to the proximal end of the extension shaft 295 opposite that of the connector 290. Linear displacement of the sliding section (e.g., slider or actuator tab) 260 is limited by the length in a longitudinal direction of the connecting arm 262; however, other conventional mechanical devices for limiting linear displacement are contemplated such as a stop element.

Figure 2B:
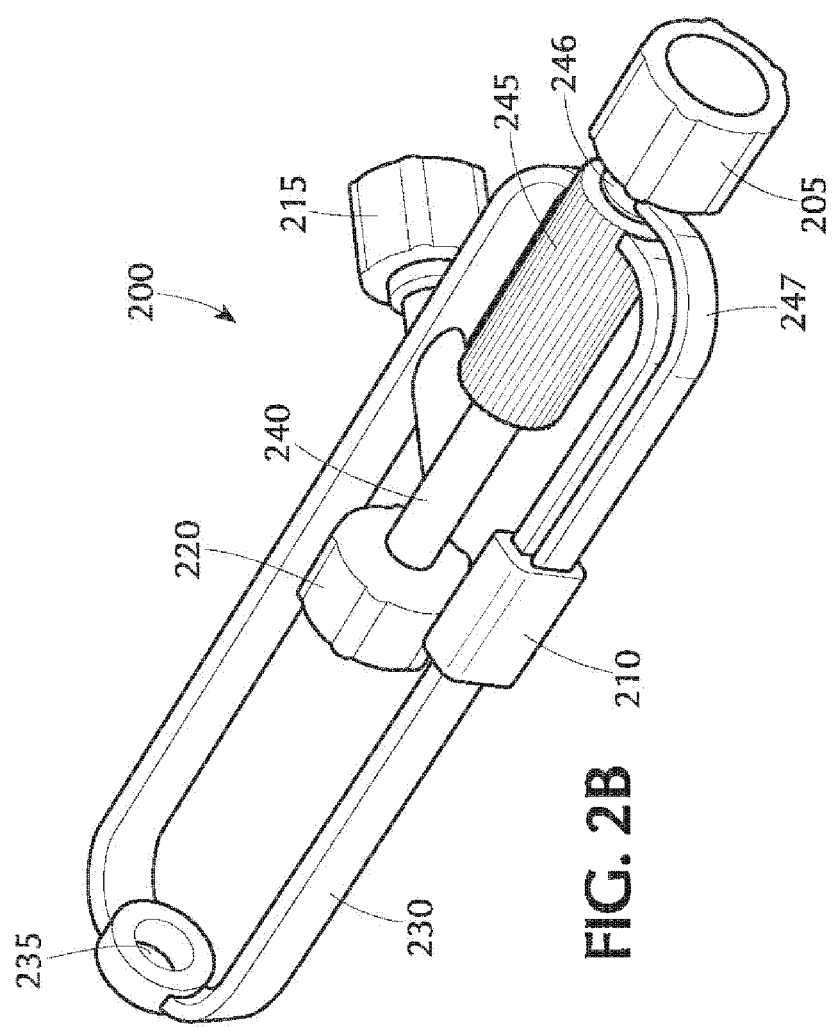
FIG. 2B is a second assist device of the assist system in accordance with the second embodiment of the present invention assembled to a second rotating hemostatic valve for controlled unsheathing ("pulling back") of the distal end of the microcatheter exposing the mechanical intravascular treatment device while simultaneously maintaining in place the guide catheter.
Figure 3:
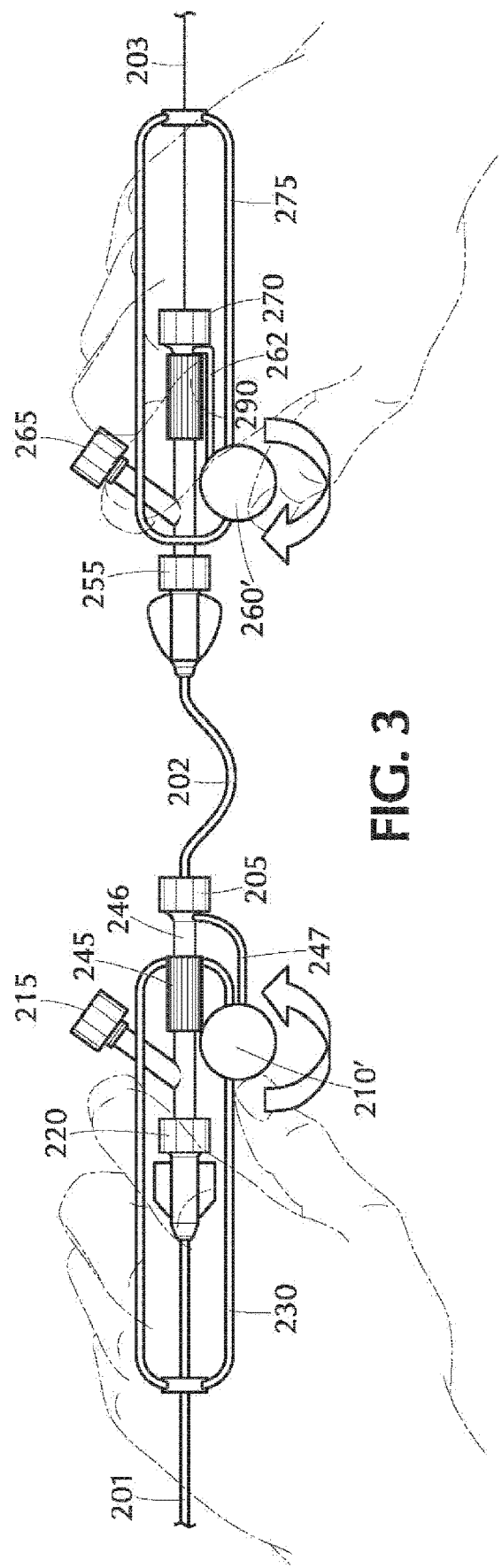
FIG. 3 illustrates two handed use of the assembled first and second assist device in accordance with an exemplary third embodiment of the present inventive assist system employing a rotating dial (e.g., thumbwheel) to impart linear movement; that is, unsheathing of the microcatheter with the left hand by manipulating the second linear sliding mechanism of the second assist device, while simultaneously pushing the delivery wire with the mechanical intravascular treatment device at its distal end with the right hand by manipulating the first linear sliding mechanism of the first assist device.

Referring to FIG. 2B, a second assist device 200 assists the interventionalist in unsheathing ("pulling back") the distal end of the microcatheter from the mechanical intravascular treatment device while maintaining the guide catheter in place. Second assist device 200 includes a second linear sliding mechanism including a second non-slidable section, i.e., a second frame 230 (similar in configuration to the first frame 275 of the first assist device). A distal end of the second frame 230 has a guide catheter receiving passageway (e.g., U-shape channel, loop or eyelet) 235 defined therein sized to allow a guide catheter to freely pass therethrough. Assembled to the second frame is a second rotating hemostatic valve or Y-valve. The second rotating hemostatic valve or Y-valve includes a guide catheter securing hub 220, an irrigation or fluid port 215, a primary shaft 240, and a connector 245 all in fluid communication with one another. In the exemplary configuration illustrated in FIG. 2B, the guide catheter securing hub 220 disposed interiorly of the second frame 230 receives and secures in place therein the guide catheter to prevent movement thereof when the microcatheter is being unsheathed. Exteriorly of the second frame 230 is a microcatheter tension device 205 securable about the outer surface of the microcatheter. Slidable along a portion of one of the longitudinal sides of the second frame 230 is a slidable section (e.g., slider or actuator tab) 210. A connecting arm 247 attaches the slidable section 210 with the microcatheter tension device 205. Connecting arm 247 is preferably disposed exteriorly/outwardly of the second frame 230 and preferably curved to substantially conform to the curved contour end of the second frame 230. Connector 245 is connected to the guide catheter securing hub 220 via a primary shaft 240. Guide catheter securing hub 220, primary shaft 240, connector 245, extension shaft 246 and microcatheter tension device 205, each have an inner channel defined therein in fluid communication with one another. Extension shaft 246 is telescopically slidable within an inner channel or passage of the connector 245 and connected to the microcatheter tension device 205. Linear displacement of the slider or actuator tab 210 is limited by the curved end of the second frame 230; however, other conventional mechanical configurations for limiting linear displacement are contemplated such as a stop component.

Figure 2C:
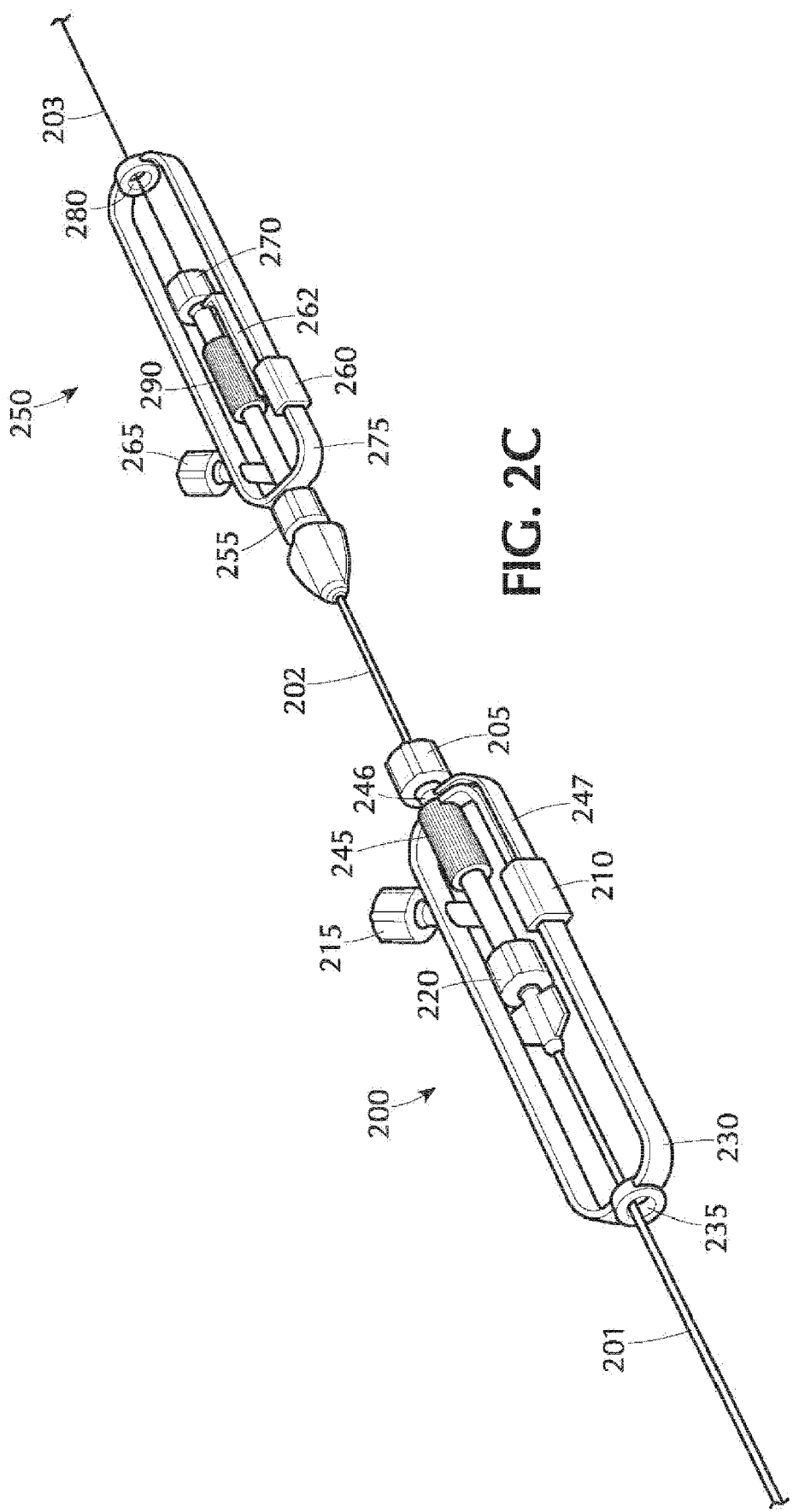
FIG. 2C is an exemplary schematic assembly of the first and second assist devices of along with their respective rotating hemostatic valves of FIGS. 2A & 2B for the exemplary assist system in accordance with the second embodiment of the present invention.

The two assist devices 200, 250 of FIGS. 2A & 2B and their respective rotating hemostatic valves assembled together as the present inventive assist system in accordance with the second embodiment is shown in FIG. 2C. Steps taken during preparation of the assist system of FIG. 2C are depicted in FIGS. 2D-2I, each of which is described below.

During operation, the proximal end of the guide catheter 201 is received through the guide catheter receiving passageway 235 (FIG. 2D) and inserted in the guide catheter securing hub 220 (while in an unlocked, unsecured, relaxed state) (FIG. 2E) of the second assist device 200, while the second linear sliding mechanism is maintained in its fully retracted state (i.e., "pushed in" towards the guide catheter receiving passageway 235 with a minimal linear displacement between the microcatheter tension device 205 and the connector 245). Detents, a catch, a pin or other mechanical component may be employed to maintain the slider 210 in the fully retracted state. By way of illustrative example, the catch, pin or other mechanical detent disposed radially outward on the extension shaft 246 may engage with an associated recess or other mating component disposed on the inner surface of the passageway of the connector 245. Guide catheter securing hub 220 is then transitioned (e.g., rotated) from an unlocked/unsecured/loosened state to a locked/secured/tensioned state securing the proximal end of the guide catheter therein, as shown in FIG. 2E.

Figure 2F:
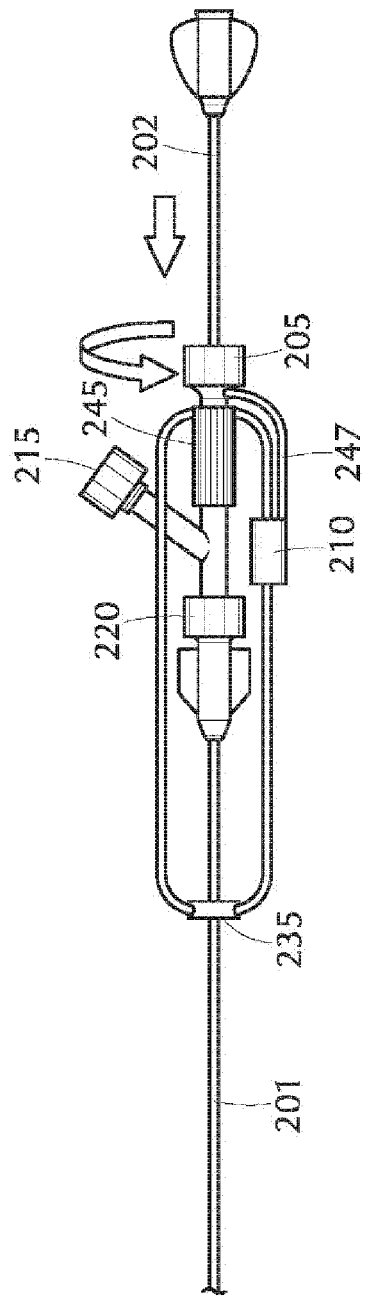
FIG. 2F depicts loosening of the microcatheter tension device associated with the second assist device to allow for insertion of the distal end of the microcatheter therein; positioning of the microcatheter to the target site within the vessel; and tightening the microcatheter tension device of the second assist device to secure the microcatheter in place.
Figure 21:
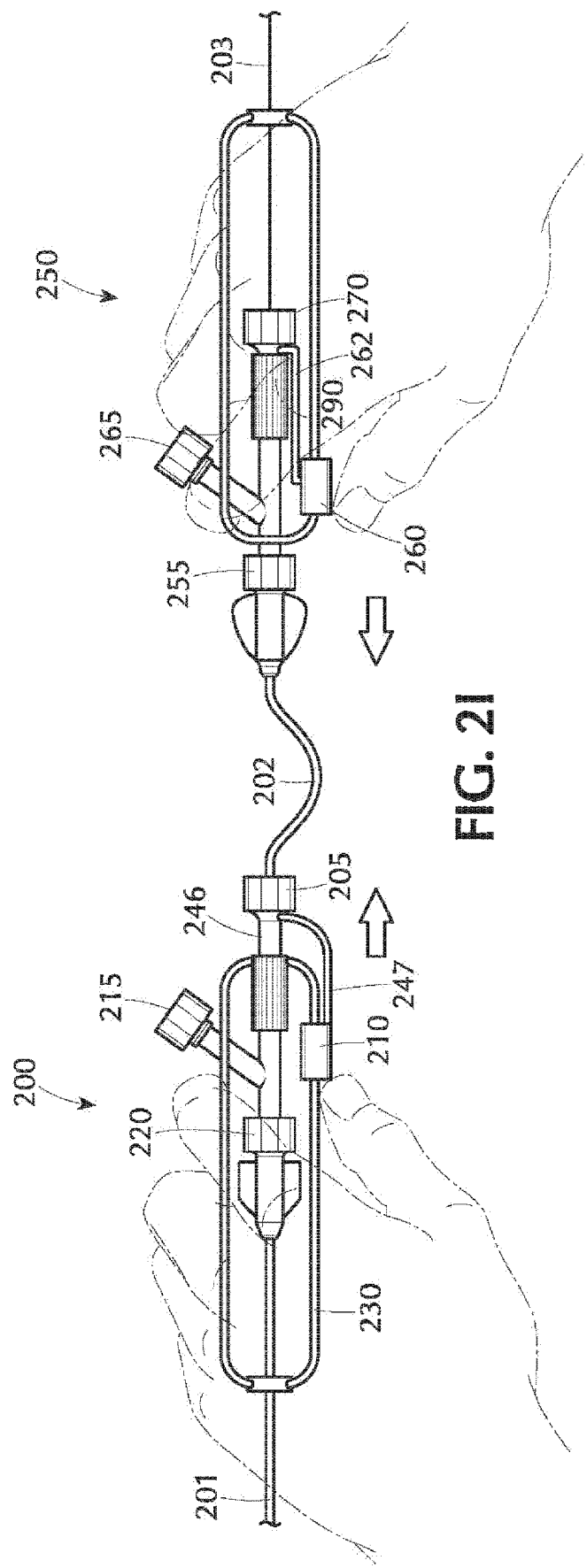

The microcatheter tension device 205 is loosened or unlocked to allow the microcatheter 202 to be advanced freely therethrough to a desired position in the lumen of the guide catheter 201. For instance, in the retrieval of a clot, the distal end of the microcatheter 202 is located on a proximal side or face of the blockage. Once the distal end of the microcatheter 202 is at the desired location within the target vessel, the microcatheter tension device 205 is transitioned (e.g., tightened by rotating) to a locked/tensioned/closed/secured position maintaining the microcatheter 202 in position, as shown in FIG. 2F.

Then, in FIG. 2G, the proximal end of the microcatheter 202 is attached to the microcatheter securing hub 255 of the first assist device 250. The linear sliding mechanism unit of the first assist device 250 is displaced in an extended state by moving the slider or actuator tab 260 in a direction away from the second assist device 200 (i.e., towards the delivery wire receiving passageway 280). In this extended state a catch, pin or other mechanical detent engages with a recess or other mechanical mating component to retain the first linear sliding mechanism of the first assist device 250 in its extended state, similar to that described above regarding the second assist device 200.

Delivery wire tension device 270 of the first assist device 250 is unlocked/loosened/released (e.g., by rotation), as shown in FIG. 2H. While subject to fluoroscopy or other imaging, using the delivery wire 203 the self-expanding mechanical intravascular treatment device disposed proximate the distal end of the delivery wire 203 is advanced in a distal direction through the lumen of the microcatheter 202 (as denoted by the arrow) until proximate the distal end of the microcatheter. Once the self-expanding mechanical vascular treatment device is properly positioned proximate a distal end of the microcatheter 202, the delivery wire tension device 270 is locked/tensioned/closed/secured (e.g., rotated) about the delivery wire 203.

At this point the microcatheter 202 and mechanical intravascular treatment device disposed at the distal end of the delivery wire 203 are properly positioned at the target site in the vessel while (i) controlled unsheathing of the distal end of the microcatheter 202 from the mechanical intravascular treatment device is realized using the second linear sliding mechanism of the second assist device 200; and (ii) controlled advancement of the mechanical intravascular treatment device using the delivery wire 203 is achieved using the first linear sliding mechanism of the first assist device. During such controlled movement, the guide catheter 201 is maintained in place via the guide catheter securing hub 220 of the second assist device 200 while the microcatheter 202 is secured in place via the microcatheter securing hub 255 of the first assist device 250.

Referring to FIG. 2I, the interventionalist with one hand displaces the slider or actuator tab 210 of the second assist device 200 in a proximal direction towards the first assist device 250 (i.e., away from the guide catheter 201) thereby unsheathing ("pulling back") the mechanical intravascular treatment device from the distal end of the microcatheter 202. During such unsheathing movement, the guide catheter is secured in place by the guide catheter securing hub 220. Simultaneously, with the other hand, the interventionalist displaces ("pushes") the slider or actuator tab 260 of the first assist device 250 in a distal direction towards the second assist device 200 thereby advancing the delivery wire 203 through the lumen of the microcatheter 202 until the self-expanding mechanical intravascular treatment device exits from the distal end of the microcatheter. No longer compressed radially by the inner walls of the lumen of the microcatheter 202, the self-expanding mechanical intravascular treatment device automatically deploys to its expanded state (enlarged diameter).

Heretofore, operation of the system in accordance with the present invention has been described for deployment of the mechanical intravascular treatment. Recapture (resheathing) of the mechanical vascular treatment device may be accomplished by performing the reverse operation to that described above. That is, with the second assist device 200 pulling in a distal direction (away from the first assist device 250) the mechanical intravascular treatment device is resheathed by the distal end of the microcatheter, while simultaneously with the right hand the delivery device (along with the mechanical vascular treatment device) is withdrawn in a proximal direction (away from the second assist device 200) compressed in diameter to be received within the lumen of the microcatheter.

FIG. 3 is still another configuration with the slider or actuator tabs 210, 260 associated with the linear sliding mechanism of each of the first and second assist device 200, 250, respectively, of FIG. 2I, replaced with a rotating dial or wheel 210', 260' (e.g., thumbwheel) in combination with a conventional rack-and-pinion gear arrangement. Although not shown it is also contemplated that the device for actuating the linear sliding mechanisms may be replaced with a lever or other linear actuating mechanism.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A system to assist delivery of a mechanical intravascular treatment device, the system comprising:
   a delivery wire;
   a first assist device comprising:
      a first linear sliding mechanism including:
         a first non-slidable section;
         a first slidable section linearly displaceable relative to the first non-slidable section; the first slidable section having a passageway in a longitudinal direction;
         an extension shaft receivable in the passageway of the first slidable section;
         a first tension device directly connected to the first slidable section to move together along the extension shaft; the first tension device being transitionable between an unsecured state and a secured state; the first tension device receives and secures therein the delivery wire; and
      a first securing hub fixedly attached to the first non-slidable section; the first securing hub being transitionable between an unsecured state and a secured state;
      wherein the delivery wire extends through the first non-slidable section, the extension shaft, the first tension device and the first securing hub;
      wherein the first non-slidable section is a first frame having parallel sides and curved opposing ends forming a loop around the extension shaft through which the delivery wire passes through; the first slidable section being linearly displaceable along a portion of one of the sides of the first frame; wherein the first slidable section includes a first slider tab connected to the first tension device via a first connecting arm.

2. The system in accordance with claim 1, wherein the first securing hub receives and secures therein a microcatheter; and wherein when the first tension device and the first securing hub are both in the secured state, controlled linear movement of the delivery wire while maintaining in place the microcatheter is achievable using the first linear sliding mechanism.

3. A system to assist delivery of a mechanical intravascular treatment device, the system comprising:
   a delivery wire;
   a first assist device comprising:
      a first linear sliding mechanism including:
         a first non-slidable section;
         a first slidable section linearly displaceable relative to the first non-slidable section; the first slidable section having a passageway in a longitudinal direction;
         an extension shaft receivable in the passageway of the first slidable section;
         a first tension device directly connected to the first slidable section to move together along the extension shaft; the first tension device being transitionable between an unsecured state and a secured state; the first tension device receives and secures therein the delivery wire; and
      a first securing hub fixedly attached to the first non-slidable section; the first securing hub being transitionable between an unsecured state and a secured state;
      wherein the delivery wire extends through the first non-slidable section, the extension shaft, the first tension device and the first securing hub;
   a second assist device including:
      a second linear sliding mechanism including:
         a second non-slidable section;
         a second slidable section; linearly displaceable relative to the second non-slidable section;
         a second tension device connected to the second slidable section to move together; the second tension device being transitionable between an unsecured state and a secured state; and
      a second securing hub fixedly attached to the second non-slidable section; the second securing hub being transitionable between an unsecured state and a secured state; wherein the first tension device receives and secures therein the delivery wire, while the first securing hub receives and secures therein a microcatheter; and wherein when the first tension device and the first securing hub are both in the secured state, controlled linear movement of the delivery wire while maintaining in place the microcatheter is achievable using the first linear sliding mechanism; wherein the second tension device receives and secures therein the microcatheter, while the second securing hub receives and secures therein a guide catheter; and wherein when the second tension device and the second securing hub are both in the secured state, controlled linear movement of the microcatheter while maintaining in place the guide catheter is achievable using the second linear sliding mechanism.

4. The system in accordance with claim 3, wherein the first linear sliding mechanism includes the extension shaft extending from one end of the first non-slidable section, and the first slidable section is telescopically slidable along at least a portion of the extension shaft.

5. The system in accordance with claim 3, wherein the first securing hub receives and secures therein a microcatheter; and wherein when the first tension device and the first securing hub are both in the secured state, controlled linear movement of the delivery wire while maintaining in place the microcatheter is achievable using the first linear sliding mechanism.

6. A system to assist delivery of a mechanical intravascular treatment device, the system comprising:
   a delivery wire;
   a first assist device comprising:
      a first linear sliding mechanism including:
         a first non-slidable section;
         a first slidable section linearly displaceable relative to the first non-slidable section; the first slidable section having a passageway in a longitudinal direction;
         an extension shaft receivable in the passageway of the first slidable section;
         a first tension device directly connected to the first slidable section to move together along the extension shaft; the first tension device being transitionable between an unsecured state and a secured state; the first tension device receives and secures therein the delivery wire; and
      a first securing hub fixedly attached to the first non-slidable section; the first securing hub being transitionable between an unsecured state and a secured state;
      wherein the delivery wire extends through the first non-slidable section, the extension shaft, the first tension device and the first securing hub;

a second assist device including:
  a second linear sliding mechanism including:
    a second non-slidable section;
    a second slidable section; linearly displaceable relative to the second non-slidable section;
    a second tension device connected to the second slidable section to move together; the second tension device being transitionable between an unsecured state and a secured state; and
    a second securing hub fixedly attached to the second non-slidable section; the second securing hub being transitionable between an unsecured state and a secured state; wherein the second non-slidable section is a second frame having parallel sides and curved opposing ends; the second slidable section being linearly displaceable along a portion of one of the sides of the second frame; wherein the second slidable section includes a second slider tab connected to the second tension device via a second connecting arm.

7. The system in accordance with claim 6, wherein the first securing hub receives and secures therein a microcatheter; and wherein when the first tension device and the first securing hub are both in the secured state, controlled linear movement of the delivery wire while maintaining in place the microcatheter is achievable using the first linear sliding mechanism.

8. A method for using a system to assist delivery of a mechanical intravascular treatment device; the system having a delivery wire; a first assist device that includes a first linear sliding mechanism; wherein the first linear sliding mechanism includes: a first non-slidable section; a first slidable section linearly displaceable relative to the first non-slidable section; the first slidable section having a passageway in a longitudinal direction; an extension shaft receivable in the passageway of the first slidable section; and a first tension device directly connected to the first slidable section to move together along the extension shaft; the first tension device being transitionable between an unsecured state and a secured state; the first tension device receives and secures therein the delivery wire; the system further including a first securing hub fixedly attached to the first non-slidable section, the first securing hub being transitionable between an unsecured state and a secured state; wherein the delivery wire extends through the first non-slidable section, the extension shaft, the first tension device and the first securing hub; the method comprising the step of:
  advancing the delivery wire through a lumen of a microcatheter until the mechanical vascular treatment delivery device disposed at a distal end of the delivery wire emerges from a distal end of the microcatheter; wherein the advancing step uses only the first linear sliding mechanism without grasping any portion of the delivery wire; wherein the first non-slidable section is a first frame having parallel sides and curved opposing ends forming a loop around the extension shaft through which the delivery wire passes through; the first slidable section being linearly displaceable along a portion of one of the sides of the first frame; wherein the first slidable section includes a first slider tab connected to the first tension device via a first connecting arm.

9. The method in accordance with claim 8, wherein the first securing hub receives and secures therein the microcatheter; and wherein when the first tension device and the first securing hub are both in the secured state, controlled movement of the delivery wire while maintaining in place the microcatheter is achievable using the first linear sliding mechanism.

10. A method for using a system to assist delivery of a mechanical intravascular treatment device; the system having a delivery wire; a first assist device that includes a first linear sliding mechanism; wherein the first linear sliding mechanism includes: a first non-slidable section; a first slidable section linearly displaceable relative to the first non-slidable section; the first slidable section having a passageway in a longitudinal direction; an extension shaft receivable in the passageway of the first slidable section; and a first tension device directly connected to the first slidable section to move together along the extension shaft; the first tension device being transitionable between an unsecured state and a secured state; the first tension device receives and secures therein the delivery wire; the system further including a first securing hub fixedly attached to the first non-slidable section, the first securing hub being transitionable between an unsecured state and a secured state; wherein the delivery wire extends through the first non-slidable section, the extension shaft, the first tension device and the first securing hub; wherein the system further includes a second assist device having a second linear sliding mechanism; wherein the second linear sliding mechanism includes: a second non-slidable section; a second slidable section; linearly displaceable relative to the second non-slidable section; a second tension device connected to the second slidable section to move together, the second tension device being transitionable between an unsecured state and a secured state; and the system further includes a second securing hub fixedly attached to the second non-slidable section; the second securing hub being transitionable between an unsecured state and a secured state; the method comprising the step of:
  advancing the delivery wire through a lumen of a microcatheter until the mechanical vascular treatment delivery device disposed at a distal end of the delivery wire emerges from a distal end of the microcatheter; wherein the advancing step uses only the first linear sliding mechanism without grasping any portion of the delivery wire; and
  simultaneously with the advancing step, unsheathing the mechanical intravascular treatment device from the distal end of the microcatheter using only the second linear sliding mechanism without grasping any portion of the microcatheter;
  wherein the first tension device receives and secures therein the delivery wire, while the first securing hub receives and secures therein the microcatheter; and wherein when the first tension device and the first securing hub are both in the secured state, controlled linear movement of the delivery wire while maintaining in place the microcatheter is achievable using the first linear sliding mechanism; wherein the second tension device receives and secures therein the microcatheter, while the second securing hub receives and secures therein a guide catheter; and wherein when the second tension device and the second securing hub are both in the secured state, controlled linear movement of the microcatheter while maintaining in place the guide catheter is achievable using the second linear sliding mechanism.

11. The method in accordance with claim 10, wherein the first linear sliding mechanism includes the extension shaft extending from one end of the first non-slidable section, and the first slidable section is slidable along at least a portion of the extension shaft.

12. The method in accordance with claim 10, wherein the first linear sliding mechanism associated with the advancing step and the second linear sliding mechanism associated with the unsheathing step are carried out by movement in respective directions towards one another to deploy the mechanical intravascular treatment device.

13. The method in accordance with claim 10, wherein the first linear sliding mechanism associated with the advancing step and the second linear sliding mechanism associated with the unsheathing step are carried out by movement in opposite directions from one another to recapture the mechanical intravascular treatment device within the microcatheter.

14. The method in accordance with claim 10, wherein the first securing hub receives and secures therein the microcatheter; and wherein when the first tension device and the first securing hub are both in the secured state, controlled movement of the delivery wire while maintaining in place the microcatheter is achievable using the first linear sliding mechanism.

15. A method for using a system to assist delivery of a mechanical intravascular treatment device; the system having a delivery wire; a first assist device that includes a first linear sliding mechanism; wherein the first linear sliding mechanism includes: a first non-slidable section; a first slidable section linearly displaceable relative to the first non-slidable section; the first slidable section having a passageway in a longitudinal direction; an extension shaft receivable in the passageway of the first slidable section; and a first tension device directly connected to the first slidable section to move together along the extension shaft; the first tension device being transitionable between an unsecured state and a secured state; the first tension device receives and secures therein the delivery wire; the system further including a first securing hub fixedly attached to the first non-slidable section, the first securing hub being transitionable between an unsecured state and a secured state; wherein the delivery wire extends through the first non-slidable section, the extension shaft, the first tension device and the first securing hub; wherein the system further includes a second assist device having a second linear sliding mechanism; wherein the second linear sliding mechanism includes: a second non-slidable section; a second slidable section; linearly displaceable relative to the second non-slidable section; a second tension device connected to the second slidable section to move together, the second tension device being transitionable between an unsecured state and a secured state; and the system further includes a second securing hub fixedly attached to the second non-slidable section; the second securing hub being transitionable between an unsecured state and a secured state; the method comprising the step of:

advancing the delivery wire through a lumen of a microcatheter until the mechanical vascular treatment delivery device disposed at a distal end of the delivery wire emerges from a distal end of the microcatheter; wherein the advancing step uses only the first linear sliding mechanism without grasping any portion of the delivery wire; and simultaneously with the advancing step, unsheathing the mechanical intravascular treatment device from the distal end of the microcatheter using only the second linear sliding mechanism without grasping any portion of the microcatheter;

wherein the second non-slidable section is a second frame having parallel sides and curved opposing ends; the second slidable section being linearly displaceable along a portion of one of the sides of the second frame; wherein the second slidable section includes a second slider tab connected to the second tension device via a second connecting arm.

16. The method in accordance with claim 15, wherein the first securing hub receives and secures therein the microcatheter; and wherein when the first tension device and the first securing hub are both in the secured state, controlled movement of the delivery wire while maintaining in place the microcatheter is achievable using the first linear sliding mechanism.

17. The method in accordance with claim 15, wherein the first linear sliding mechanism associated with the advancing step and the second linear sliding mechanism associated with the unsheathing step are carried out by movement in respective directions towards one another to deploy the mechanical intravascular treatment device.

18. The method in accordance with claim 15, wherein the first linear sliding mechanism associated with the advancing step and the second linear sliding mechanism associated with the unsheathing step are carried out by movement in opposite directions from one another to recapture the mechanical intravascular treatment device within the microcatheter.

* * * * *